(12) United States Patent
Kolatkar et al.

(10) Patent No.: US 8,226,977 B2
(45) Date of Patent: Jul. 24, 2012

(54) PHARMACEUTICAL COMPOSITION CONTAINING IRBESARTAN

(75) Inventors: Gershon Kolatkar, Petach Tiqva (IL); Erela Zisman, Richon le Zion (IL)

(73) Assignee: Teva Pharmaceutical Industries Ltd., Petach Tiqva (IL)

( * ) Notice: Subject to any disclaimer, the term of this patent is extended or adjusted under 35 U.S.C. 154(b) by 0 days.

(21) Appl. No.: 11/143,556

(22) Filed: Jun. 2, 2005

(65) Prior Publication Data

US 2005/0271720 A1 Dec. 8, 2005

Related U.S. Application Data

(60) Provisional application No. 60/577,427, filed on Jun. 4, 2004.

(51) Int. Cl.
*A61K 9/20* (2006.01)
(52) U.S. Cl. ...................................... 424/464
(58) Field of Classification Search ............... 514/223.5, 514/223.2; 424/464
See application file for complete search history.

(56) References Cited

U.S. PATENT DOCUMENTS

| | | | |
|---|---|---|---|
| 4,327,080 A | 4/1982 | Wong et al. |
| 4,808,413 A | 2/1989 | Joshi et al. |
| 4,879,303 A | 11/1989 | Davison et al. |
| 5,002,776 A | 3/1991 | Geoghegan et al. |
| 5,032,578 A | 7/1991 | Horovitz |
| 5,049,394 A | 9/1991 | Howard et al. |
| 5,089,626 A | 2/1992 | King |
| 5,098,889 A | 3/1992 | Costall et al. |
| 5,137,902 A | 8/1992 | Carini |
| 5,140,012 A | 8/1992 | McGovern et al. |
| 5,212,165 A | 5/1993 | Aberg et al. |
| 5,268,375 A | 12/1993 | Bernhart et al. |
| 5,270,317 A | 12/1993 | Bernhart et al. |
| 5,274,104 A | 12/1993 | Arnaud et al. |
| 5,298,497 A | 3/1994 | Tschollar et al. |
| 5,352,788 A | 10/1994 | Bernhart et al. |
| 5,393,531 A | 2/1995 | Gerhard et al. |
| 5,424,450 A | 6/1995 | Boswell et al. |
| 5,434,167 A | 7/1995 | Ferrari et al. |
| 5,457,112 A | 10/1995 | Cremer et al. |
| 5,461,039 A | 10/1995 | Tschollar et al. |
| 5,464,633 A | 11/1995 | Conte et al. |
| 5,464,854 A | 11/1995 | dePadova |
| 5,468,764 A | 11/1995 | Heitsch et al. |
| 5,472,711 A | 12/1995 | Baichwal |
| 5,472,967 A | 12/1995 | Hoornaert et al. |
| 5,498,421 A | 3/1996 | Grinstaff et al. |
| 5,501,861 A | 3/1996 | Makino et al. |
| 5,512,681 A | 4/1996 | Boswell et al. |
| 5,514,670 A | 5/1996 | Friedman et al. |
| 5,523,095 A | 6/1996 | Wilson et al. |
| 5,536,505 A | 7/1996 | Wilson et al. |
| 5,541,209 A | 7/1996 | Spinale |
| 5,559,233 A | 9/1996 | Bernhart et al. |
| 5,585,394 A | 12/1996 | Di Malta et al. |
| 5,593,971 A | 1/1997 | Tschollar et al. |
| 5,603,943 A | 2/1997 | Yanagawa |
| 5,612,359 A | 3/1997 | Murugesan |
| 5,622,985 A | 4/1997 | Olukotun et al. |
| 5,629,331 A | 5/1997 | Caron et al. |
| 5,645,839 A | 7/1997 | Chobanian et al. |
| 5,696,145 A | 12/1997 | Foulon et al. |
| 5,707,644 A | 1/1998 | Illum |
| 5,707,648 A | 1/1998 | Yiv |
| 5,744,166 A | 4/1998 | Illum |
| 5,753,651 A | 5/1998 | dePadova |
| 5,780,473 A | 7/1998 | Murugesan et al. |
| 5,788,987 A | 8/1998 | Busetti et al. |
| 5,804,212 A | 9/1998 | Illum |
| 5,814,336 A | 9/1998 | Kelm et al. |
| 5,824,696 A | 10/1998 | Griswold et al. |
| 5,830,909 A | 11/1998 | Crandall |
| 5,846,985 A | 12/1998 | Murugesan |
| 5,846,990 A | 12/1998 | Murugesan |
| 5,889,020 A | 3/1999 | Huxley et al. |
| 5,891,469 A | 4/1999 | Amselem |
| 5,900,428 A | 5/1999 | Fandriks et al. |
| 5,914,132 A | 6/1999 | Kelm et al. |
| 5,916,907 A | 6/1999 | Bird |
| 5,939,446 A | 8/1999 | Murugesan et al. |
| 5,985,915 A | 11/1999 | Frangin et al. |

(Continued)

FOREIGN PATENT DOCUMENTS

EP 0532410 A1 3/1993

(Continued)

OTHER PUBLICATIONS

Science lab.com, 1 page, 1997.* European Patent Office, Supplementary European Search Report in European Patent Application No. 05775601.7 (Apr. 24, 2008).
European Patent Office, Examination Report in European Patent Application No. 05775601.7 (Sep. 16, 2008).
IP Australia, Examination Report in Australian Patent Application No. 2005249794 (Mar. 23, 2010).
U.S. Food and Drug Administration, "Avapro (irbesartan) tablets," FDA Online (Oct. 4, 2003) (retrieved from the internet on Apr. 24, 2008, http://www.fda.gov/cder/foi/label/2001/20757s11lbl.pdf).
U.S. Food and Drug Administration, "Web Search," FDA Online (Apr. 24, 2008) (retrieved from the internet on Apr. 24, 2008, http://google2.fda.gov/search?q=poloxamer&btnG&sort=date%3AD%3AL%3Ad1&ie=UTF-8&proxystylesheet=FDA& x=0>).

(Continued)

*Primary Examiner* — Brandon Fetterolf
*Assistant Examiner* — Shirley V Gembeh
(74) *Attorney, Agent, or Firm* — Leydig, Voit & Mayer, Ltd.

(57) ABSTRACT

This invention relates to pharmaceutical compositions containing irbesartan, providing oral formulations with a high relative amount or concentration of irbesartan. In one embodiment, the present invention provides an oral formulation of irbesartan containing greater than 70% w/w irbesartan. In another embodiment, the invention provides an oral formulation of irbesartan which exhibits a dissolution profile according to which greater than about 85% of the Irbesartan is dissolved within about 30 minutes using USP apparatus 2, placing the tablet in 1000 mL of 0.1N hydrochloric acid at 37° C. with paddle speed of 50 rpm. The formulation can optionally contain at least one additional active ingredient.

26 Claims, No Drawings

U.S. PATENT DOCUMENTS

| | | | |
|---|---|---|---|
| 5,994,348 A | * | 11/1999 | Ku et al. .................. 514/223.5 |
| 5,994,350 A | | 11/1999 | Foulon et al. |
| 6,010,716 A | | 1/2000 | Saunal et al. |
| 6,019,988 A | | 2/2000 | Parab et al. |
| 6,025,380 A | | 2/2000 | Hill |
| 6,028,091 A | | 2/2000 | Hill |
| 6,034,114 A | | 3/2000 | Hill |
| 6,043,265 A | | 3/2000 | Murugesan et al. |
| 6,051,594 A | * | 4/2000 | Lowrey ......................... 514/400 |
| 6,057,139 A | * | 5/2000 | Kulkarni et al. ............. 435/188 |
| 6,090,818 A | | 7/2000 | Foulon et al. |
| 6,096,772 A | | 8/2000 | Fandriks et al. |
| 6,127,370 A | | 10/2000 | Smith et al. |
| 6,162,922 A | | 12/2000 | Anderson et al. |
| 6,162,923 A | | 12/2000 | Huszar et al. |
| 6,174,910 B1 | | 1/2001 | De Gasparo et al. |
| 6,174,917 B1 | | 1/2001 | McLean |
| 6,183,780 B1 | | 2/2001 | Van Balken et al. |
| 6,187,336 B1 | | 2/2001 | Okumura et al. |
| 6,201,002 B1 | | 3/2001 | Beere et al. |
| 6,218,414 B1 | | 4/2001 | Nisato |
| 6,248,358 B1 | | 6/2001 | Bologna et al. |
| 6,248,363 B1 | | 6/2001 | Patel et al. |
| 6,248,729 B1 | | 6/2001 | Coniglio et al. |
| 6,264,914 B1 | | 7/2001 | Klaveness et al. |
| 6,264,981 B1 | | 7/2001 | Zhang et al. |
| 6,267,990 B1 | | 7/2001 | Fischer et al. |
| 6,271,375 B1 | | 8/2001 | Villa et al. |
| 6,284,277 B1 | | 9/2001 | Bouloumie et al. |
| 6,284,363 B1 | | 9/2001 | Maeda et al. |
| 6,284,763 B1 | | 9/2001 | Adams et al. |
| 6,298,192 B1 | | 10/2001 | Yoo et al. |
| 6,300,356 B1 | | 10/2001 | Segal et al. |
| 6,309,663 B1 | | 10/2001 | Patel et al. |
| 6,323,226 B1 | | 11/2001 | Delgado, III et al. |
| 6,335,451 B1 | | 1/2002 | Kleemann et al. |
| 6,339,085 B1 | | 1/2002 | Haque |
| 6,342,247 B1 | | 1/2002 | Ku et al. |
| 6,358,983 B1 | | 3/2002 | Amberg et al. |
| 6,383,471 B1 | | 5/2002 | Chen et al. |
| 6,387,894 B1 | | 5/2002 | Fossa |
| 6,414,002 B1 | | 7/2002 | Cheng et al. |
| 6,414,126 B1 | | 7/2002 | Ellsworth et al. |
| 6,417,204 B1 | | 7/2002 | Haque |
| 6,420,426 B1 | | 7/2002 | Van Zandt |
| 6,448,280 B1 | | 9/2002 | Carey et al. |
| 6,451,339 B2 | | 9/2002 | Patel et al. |
| 6,458,797 B1 | | 10/2002 | Adams et al. |
| 6,465,463 B1 | | 10/2002 | Cohn et al. |
| 6,469,024 B2 | | 10/2002 | Li et al. |
| 6,475,510 B1 | * | 11/2002 | Venkatesh et al. ............. 424/441 |
| 6,482,517 B1 | | 11/2002 | Anderson |
| 6,485,726 B1 | | 11/2002 | Blumberg et al. |
| 6,486,188 B1 | | 11/2002 | Pedersen et al. |
| 6,489,307 B1 | | 12/2002 | Phillips et al. |
| 6,495,581 B1 | | 12/2002 | Momose et al. |
| 6,515,117 B2 | | 2/2003 | Ellsworth et al. |
| 6,521,659 B2 | | 2/2003 | Sredy et al. |
| 6,531,152 B1 | | 3/2003 | Lerner et al. |
| 6,544,981 B2 | | 4/2003 | Stein et al. |
| 6,548,529 B1 | | 4/2003 | Robl et al. |
| 6,555,542 B1 | | 4/2003 | O'Connor et al. |
| 6,555,551 B1 | | 4/2003 | Spireas |
| 6,555,568 B1 | | 4/2003 | Sredy et al. |
| 6,569,463 B2 | | 5/2003 | Patel et al. |
| 6,570,013 B2 | | 5/2003 | Mylari |
| 6,576,256 B2 | | 6/2003 | Liang et al. |
| 6,579,879 B2 | | 6/2003 | Mylari |
| 6,586,004 B2 | | 7/2003 | Shimizu et al. |
| 6,589,547 B1 | | 7/2003 | Igari et al. |
| 6,589,556 B2 | | 7/2003 | Cherukuri |
| 6,592,901 B2 | | 7/2003 | Durig et al. |
| 6,595,926 B1 | | 7/2003 | Laragh |
| 6,596,744 B2 | | 7/2003 | Wagle et al. |
| 6,604,698 B2 | | 8/2003 | Verhoff et al. |
| 6,610,682 B2 | | 8/2003 | Tsujita et al. |
| 6,627,649 B1 | | 9/2003 | Lacour et al. |
| 6,632,180 B1 | | 10/2003 | Laragh |
| 6,632,451 B2 | | 10/2003 | Penhasi et al. |
| 6,634,576 B2 | | 10/2003 | Verhoff et al. |
| 6,635,273 B1 | | 10/2003 | Loscalzo et al. |
| 6,635,279 B2 | | 10/2003 | Kolter et al. |
| 6,638,937 B2 | | 10/2003 | Murugesan et al. |
| 6,642,244 B2 | | 11/2003 | Macor et al. |
| 6,645,463 B1 | | 11/2003 | Counsell et al. |
| 6,653,306 B1 | | 11/2003 | Alexander et al. |
| 6,656,966 B2 | | 12/2003 | Garvey et al. |
| 6,669,955 B2 | | 12/2003 | Chungi et al. |
| 6,670,380 B2 | | 12/2003 | Sulski et al. |
| 6,670,386 B2 | | 12/2003 | Sun et al. |
| 6,673,815 B2 | | 1/2004 | Devasthale et al. |
| 6,673,824 B1 | | 1/2004 | Murugesan et al. |
| 6,677,356 B1 | | 1/2004 | Sethi et al. |
| 6,685,962 B2 | | 2/2004 | Friedman et al. |
| 6,720,001 B2 | | 4/2004 | Chen et al. |
| 6,800,761 B1 | * | 10/2004 | Franc et al. .................. 548/253 |
| 2001/0009678 A1 | | 7/2001 | Toshihiro et al. |
| 2001/0010825 A1 | | 8/2001 | Shimizu et al. |
| 2001/0016587 A1 | | 8/2001 | Klaveness et al. |
| 2001/0016594 A1 | | 8/2001 | Hill |
| 2001/0031770 A1 | | 10/2001 | Haque |
| 2001/0038852 A1 | | 11/2001 | Kolter et al. |
| 2001/0041722 A1 | | 11/2001 | Sredy et al. |
| 2001/0044584 A1 | | 11/2001 | Kensey et al. |
| 2001/0056095 A1 | | 12/2001 | Mylari |
| 2002/0003179 A1 | | 1/2002 | Verhoff et al. |
| 2002/0004500 A1 | | 1/2002 | Reeves et al. |
| 2002/0006440 A1 | | 1/2002 | Cherukuri |
| 2002/0010146 A1 | | 1/2002 | Garvey et al. |
| 2002/0010158 A1 | | 1/2002 | Haque |
| 2002/0012680 A1 | | 1/2002 | Patel et al. |
| 2002/0012701 A1 | | 1/2002 | Kolter et al. |
| 2002/0013308 A1 | | 1/2002 | Tsujita et al. |
| 2002/0013334 A1 | | 1/2002 | Robl et al. |
| 2002/0013335 A1 | | 1/2002 | Azrolan et al. |
| 2002/0016364 A1 | | 2/2002 | Luchoomun et al. |
| 2002/0019360 A1 | | 2/2002 | Kivlighn et al. |
| 2002/0022587 A1 | | 2/2002 | Ferguson et al. |
| 2002/0022637 A1 | | 2/2002 | Li et al. |
| 2002/0025957 A1 | | 2/2002 | Stein et al. |
| 2002/0028826 A1 | | 3/2002 | Robl et al. |
| 2002/0032149 A1 | | 3/2002 | Kensey |
| 2002/0034474 A1 | | 3/2002 | Sabel et al. |
| 2002/0035067 A1 | | 3/2002 | Adams et al. |
| 2002/0044960 A1 | | 4/2002 | Cherukuri |
| 2002/0044962 A1 | | 4/2002 | Cherukuri |
| 2002/0045616 A1 | | 4/2002 | Stein et al. |
| 2002/0047058 A1 | | 4/2002 | Verhoff et al. |
| 2002/0048599 A1 | | 4/2002 | Mueller |
| 2002/0049155 A1 | | 4/2002 | Hogenkamp et al. |
| 2002/0061835 A1 | | 5/2002 | Kensey et al. |
| 2002/0061901 A1 | | 5/2002 | Robl et al. |
| 2002/0068729 A1 | | 6/2002 | Egan et al. |
| 2002/0068740 A1 | | 6/2002 | Mylari |
| 2002/0076437 A1 | | 6/2002 | Kothari et al. |
| 2002/0077340 A1 | | 6/2002 | Sulski et al. |
| 2002/0082285 A1 | | 6/2002 | Lebwohl |
| 2002/0091078 A1 | | 7/2002 | Sulski et al. |
| 2002/0094346 A1 | | 7/2002 | Lin et al. |
| 2002/0094977 A1 | | 7/2002 | Robl et al. |
| 2002/0099046 A1 | | 7/2002 | Scott |
| 2002/0107236 A1 | | 8/2002 | Sahota |
| 2002/0107245 A1 | | 8/2002 | Wagle et al. |
| 2002/0107265 A1 | | 8/2002 | Chen et al. |
| 2002/0110593 A1 | | 8/2002 | Penhasi et al. |
| 2002/0132822 A1 | | 9/2002 | Noe et al. |
| 2002/0133008 A1 | | 9/2002 | Macor et al. |
| 2002/0137755 A1 | | 9/2002 | Bilodeau et al. |
| 2002/0137903 A1 | | 9/2002 | Ellsworth et al. |
| 2002/0143017 A1 | | 10/2002 | Mylari |
| 2002/0143024 A1 | | 10/2002 | Murugesan et al. |
| 2002/0143176 A1 | | 10/2002 | Liu et al. |
| 2002/0147184 A1 | | 10/2002 | Kosoglou et al. |
| 2002/0151536 A1 | | 10/2002 | Davis et al. |
| 2002/0155432 A1 | | 10/2002 | Schwartz et al. |
| 2002/0156089 A1 | | 10/2002 | Chen |
| 2002/0168393 A1 | | 11/2002 | Sugimoto |

| | | |
|---|---|---|
| 2002/0169174 A1 | 11/2002 | Chackalamannil et al. |
| 2002/0177586 A1 | 11/2002 | Egan et al. |
| 2002/0177587 A1 | 11/2002 | Bi et al. |
| 2002/0182605 A1 | 12/2002 | Anastasio et al. |
| 2002/0182681 A1 | 12/2002 | Woodage et al. |
| 2002/0183260 A1 | 12/2002 | Fink |
| 2002/0183305 A1 | 12/2002 | Davis et al. |
| 2002/0183317 A1 | 12/2002 | Wagle et al. |
| 2002/0183365 A1 | 12/2002 | Wagle et al. |
| 2002/0187188 A1 | 12/2002 | Cherukuri |
| 2002/0187939 A1 | 12/2002 | Montgomery et al. |
| 2002/0192203 A1 | 12/2002 | Cho et al. |
| 2002/0192222 A1 | 12/2002 | Blumberg et al. |
| 2003/0003470 A1 | 1/2003 | Salonen |
| 2003/0004139 A1 | 1/2003 | Martin et al. |
| 2003/0004166 A1 | 1/2003 | Mylari |
| 2003/0004168 A1 | 1/2003 | Prevost et al. |
| 2003/0004194 A1 | 1/2003 | Gall |
| 2003/0004199 A1 | 1/2003 | Ounis |
| 2003/0008020 A1 | 1/2003 | Adams et al. |
| 2003/0012789 A1 | 1/2003 | Blumberg et al. |
| 2003/0021845 A1 | 1/2003 | Friedman et al. |
| 2003/0021846 A1 | 1/2003 | Kolter et al. |
| 2003/0022890 A1 | 1/2003 | Atwal et al. |
| 2003/0027820 A1 | 2/2003 | Gall |
| 2003/0036558 A1 | 2/2003 | Van Zandt |
| 2003/0040516 A1 | 2/2003 | Sulsky et al. |
| 2003/0045460 A1 | 3/2003 | Fogelman et al. |
| 2003/0049314 A1 | 3/2003 | Liang et al. |
| 2003/0050301 A1 | 3/2003 | Mylari |
| 2003/0050305 A1 | 3/2003 | Tejada |
| 2003/0050620 A1 | 3/2003 | Odidi et al. |
| 2003/0053981 A1 | 3/2003 | Davis et al. |
| 2003/0055039 A1 | 3/2003 | Ikeya et al. |
| 2003/0055094 A1 | 3/2003 | Sun et al. |
| 2003/0055258 A2 | 3/2003 | Filic et al. |
| 2003/0060451 A1 | 3/2003 | Taneja et al. |
| 2003/0064097 A1 | 4/2003 | Patel et al. |
| 2003/0064935 A1 | 4/2003 | Gougoutas |
| 2003/0064937 A1 | 4/2003 | Nieuwenhuizen et al. |
| 2003/0068366 A1 | 4/2003 | Chungi et al. |
| 2003/0068374 A1 | 4/2003 | Kamei et al. |
| 2003/0069169 A1 | 4/2003 | Macor et al. |
| 2003/0069221 A1 | 4/2003 | Kosoglou et al. |
| 2003/0069275 A1 | 4/2003 | Cheng et al. |
| 2003/0073656 A1 | 4/2003 | Waltz et al. |
| 2003/0073705 A1 | 4/2003 | Shahinfar et al. |
| 2003/0073708 A1 | 4/2003 | Castelhano et al. |
| 2003/0073729 A1 | 4/2003 | Kitahara et al. |
| 2003/0077229 A1 | 4/2003 | Dugger |
| 2003/0077297 A1 | 4/2003 | Chen et al. |
| 2003/0077327 A1 | 4/2003 | Durig et al. |
| 2003/0078190 A1 | 4/2003 | Weinberg |
| 2003/0078517 A1 | 4/2003 | Kensey |
| 2003/0083286 A1 | 5/2003 | Teng et al. |
| 2003/0083339 A1 | 5/2003 | Tamura |
| 2003/0083342 A1 | 5/2003 | Steele |
| 2003/0083614 A1 | 5/2003 | Eisert |
| 2003/0087843 A1 | 5/2003 | Washburn |
| 2003/0087935 A1 | 5/2003 | Cheng et al. |
| 2003/0092697 A1 | 5/2003 | Cheng et al. |
| 2003/0092732 A1 | 5/2003 | Yu et al. |
| 2003/0092736 A1 | 5/2003 | Cheng et al. |
| 2003/0096782 A1 | 5/2003 | Bristow et al. |
| 2003/0096803 A1 | 5/2003 | Noe et al. |
| 2003/0096827 A1 | 5/2003 | Yu et al. |
| 2003/0096846 A1 | 5/2003 | Cheng et al. |
| 2003/0104048 A1 | 6/2003 | Patel et al. |
| 2003/0113330 A1 | 6/2003 | Uhal |
| 2003/0114357 A1 | 6/2003 | Fryburg et al. |
| 2003/0114382 A1 | 6/2003 | Walsh |
| 2003/0114390 A1 | 6/2003 | Washburn et al. |
| 2003/0114420 A1 | 6/2003 | Salvati et al. |
| 2003/0114469 A1 | 6/2003 | Cohen |
| 2003/0114677 A1 | 6/2003 | Haque |
| 2003/0114678 A1 | 6/2003 | Haque |
| 2003/0119010 A1 | 6/2003 | Powell et al. |
| 2003/0119428 A1 | 6/2003 | Davis et al. |
| 2003/0119796 A1 | 6/2003 | Strony |
| 2003/0119808 A1 | 6/2003 | LeBeaut et al. |
| 2003/0120074 A1 | 6/2003 | Haque |
| 2003/0124182 A1 | 7/2003 | Shojaei et al. |
| 2003/0124184 A1 | 7/2003 | Mezaache et al. |
| 2003/0124196 A1 | 7/2003 | Weinbach et al. |
| 2003/0130306 A1 | 7/2003 | Devasthale et al. |
| 2003/0134810 A1 | 7/2003 | Springate et al. |
| 2003/0134884 A1 | 7/2003 | Hazama et al. |
| 2003/0139429 A1 | 7/2003 | Cohen |
| 2003/0144198 A1 | 7/2003 | Collins |
| 2003/0144206 A1 | 7/2003 | Knudsen et al. |
| 2003/0144269 A1 | 7/2003 | Block |
| 2003/0144270 A1 | 7/2003 | Reichard et al. |
| 2003/0144287 A1 | 7/2003 | Quan |
| 2003/0144298 A1 | 7/2003 | Curwen et al. |
| 2003/0144338 A1 | 7/2003 | Matsumoto et al. |
| 2003/0149058 A1 | 8/2003 | Eisert |
| 2003/0149070 A1 | 8/2003 | Azrolan et al. |
| 2003/0152622 A1 | 8/2003 | Louie-Helm et al. |
| 2003/0152636 A1 | 8/2003 | Sabel et al. |
| 2003/0152824 A1 | 8/2003 | Kasuga et al. |
| 2003/0153587 A1 | 8/2003 | Asberom et al. |
| 2003/0158090 A1 | 8/2003 | Pedersen-Bjergaard et al. |
| 2003/0158173 A1 | 8/2003 | Paliwal et al. |
| 2003/0158177 A1 | 8/2003 | Ishihara et al. |
| 2003/0158223 A1 | 8/2003 | Anderson et al. |
| 2003/0158232 A1 | 8/2003 | Cheng et al. |
| 2003/0162759 A1 | 8/2003 | Rocha et al. |
| 2003/0162784 A1 | 8/2003 | Mylari |
| 2003/0162828 A1 | 8/2003 | Schlesinger |
| 2003/0166189 A1 | 9/2003 | Woodage et al. |
| 2003/0166668 A1 | 9/2003 | Zandt et al. |
| 2003/0166724 A1 | 9/2003 | Hangeland |
| 2003/0171287 A1 | 9/2003 | Morishita et al. |
| 2003/0171405 A1 | 9/2003 | Sredy et al. |
| 2003/0171415 A1 | 9/2003 | Boehm et al. |
| 2003/0175344 A1 | 9/2003 | Wald et al. |
| 2003/0176413 A1 | 9/2003 | Asberom et al. |
| 2003/0176426 A1 | 9/2003 | Wagle et al. |
| 2003/0180352 A1 | 9/2003 | Patel et al. |
| 2003/0180359 A1 | 9/2003 | Vergnault et al. |
| 2003/0181422 A1 | 9/2003 | Haque |
| 2003/0181500 A1 | 9/2003 | Lee et al. |
| 2003/0181728 A1 | 9/2003 | Salvati et al. |
| 2003/0186985 A1 | 10/2003 | Momose et al. |
| 2003/0187038 A1 | 10/2003 | Imura et al. |
| 2003/0187254 A1 | 10/2003 | Perry et al. |
| 2003/0191057 A1 | 10/2003 | Fogelman et al. |
| 2003/0191115 A1 | 10/2003 | Pinto et al. |
| 2003/0195157 A1 | 10/2003 | Natarajan et al. |
| 2003/0195205 A1 | 10/2003 | DeNinno et al. |
| 2003/0195236 A1 | 10/2003 | Haque |
| 2003/0198676 A1 | 10/2003 | Igari et al. |
| 2003/0199424 A1 | 10/2003 | Smith et al. |
| 2003/0199492 A1 | 10/2003 | Scott |
| 2003/0199563 A1 | 10/2003 | Robl et al. |
| 2003/0203019 A1 | 10/2003 | Cornelius et al. |
| 2003/0203027 A1 | 10/2003 | Verreck et al. |
| 2003/0203915 A1 | 10/2003 | Fang et al. |
| 2003/0206978 A1 | 11/2003 | Sherwood et al. |
| 2003/0207925 A1 | 11/2003 | Cameron et al. |
| 2003/0212054 A1 | 11/2003 | Quan et al. |
| 2003/0212072 A1 | 11/2003 | Mylari |
| 2003/0212124 A1 | 11/2003 | Kevorkian |
| 2003/0215496 A1 | 11/2003 | Patel et al. |
| 2003/0215526 A1 | 11/2003 | Stofik et al. |
| 2003/0216384 A1 | 11/2003 | Stokes |
| 2003/0216424 A1 | 11/2003 | Davis |
| 2003/0216452 A1 | 11/2003 | Sredy et al. |
| 2003/0216476 A1 | 11/2003 | Kleemann |
| 2003/0220297 A1 | 11/2003 | Berstein et al. |
| 2003/0221207 A1 | 11/2003 | McMahon et al. |
| 2003/0225056 A1 | 12/2003 | Freeman-Cook et al. |
| 2003/0225091 A1 | 12/2003 | Magnin et al. |
| 2003/0225110 A1 | 12/2003 | Zhou et al. |
| 2003/0225124 A1 | 12/2003 | Spireas |
| 2003/0225128 A1 | 12/2003 | Bi et al. |
| 2003/0225146 A1 | 12/2003 | Wagle et al. |
| 2003/0228254 A1 | 12/2003 | Klaveness et al. |

| | | | |
|---|---|---|---|
| 2003/0228371 A1 | 12/2003 | Skinner et al. | |
| 2003/0229007 A1 | 12/2003 | Levi et al. | |
| 2003/0229015 A1 | 12/2003 | Fogelman et al. | |
| 2003/0232073 A1 | 12/2003 | Houze et al. | |
| 2003/0232081 A1 | 12/2003 | Doshi et al. | |
| 2003/0232796 A1 | 12/2003 | Cooper et al. | |
| 2003/0232804 A1 | 12/2003 | Pinto et al. | |
| 2003/0232809 A1 | 12/2003 | Terashita et al. | |
| 2003/0232845 A1 | 12/2003 | Dahanukar et al. | |
| 2003/0232849 A1 | 12/2003 | Noe et al. | |
| 2003/0232866 A1 | 12/2003 | Watterson et al. | |
| 2003/0233118 A1 | 12/2003 | Hui | |
| 2003/0235536 A1 | 12/2003 | Blumberg et al. | |
| 2003/0235595 A1 | 12/2003 | Chen et al. | |
| 2004/0002495 A1 | 1/2004 | Sher et al. | |
| 2004/0005306 A1 | 1/2004 | Loscalzo et al. | |
| 2004/0005358 A1 | 1/2004 | Slugg et al. | |
| 2004/0006057 A1 | 1/2004 | Reiter et al. | |
| 2004/0006062 A1 | 1/2004 | Smallheer et al. | |
| 2004/0006119 A1 | 1/2004 | Lang et al. | |
| 2004/0009972 A1 | 1/2004 | Ding et al. | |
| 2004/0010141 A1 | 1/2004 | Noe et al. | |
| 2004/0014782 A1 | 1/2004 | Krause | |
| 2004/0015134 A1 | 1/2004 | Lavi et al. | |
| 2004/0018239 A1 | 1/2004 | Ishida et al. | |
| 2004/0018240 A1 | 1/2004 | Ohmachi et al. | |
| 2004/0019063 A1 | 1/2004 | Sun et al. | |
| 2004/0019085 A1 | 1/2004 | Slusarchyk et al. | |
| 2004/0023840 A1 | 2/2004 | De Gasparo et al. | |
| 2004/0023967 A1 | 2/2004 | Cohn et al. | |
| 2004/0024216 A1 | 2/2004 | Robl et al. | |
| 2004/0033992 A1 | 2/2004 | Sethi et al. | |
| 2004/0033993 A1 | 2/2004 | Sethi et al. | |
| 2004/0034001 A1 | 2/2004 | Karara | |
| 2004/0038945 A1 | 2/2004 | Sethi et al. | |
| 2004/0062802 A1 | 4/2004 | Hermelin | |
| 2004/0063646 A1 | 4/2004 | Fujikura et al. | |
| 2004/0077723 A1 | 4/2004 | Granata et al. | |
| 2004/0081642 A1 | 4/2004 | Loscalzo et al. | |
| 2004/0087484 A1 | 5/2004 | Sahota | |
| 2004/0096499 A1 | 5/2004 | Vaya et al. | |
| 2004/0106953 A1 | 6/2004 | Yomtov et al. | |
| 2004/0106954 A1 | 6/2004 | Whitehurst et al. | |
| 2004/0116357 A1 | 6/2004 | Fushimi et al. | |
| 2004/0116510 A1 | 6/2004 | Nichtberger | |
| 2004/0132669 A1 | 7/2004 | Nishimura et al. | |
| 2004/0132805 A1 | 7/2004 | Garvey | |
| 2004/0138148 A1 | 7/2004 | Fushimi et al. | |
| 2004/0138306 A1 | 7/2004 | Guth et al. | |
| 2004/0141925 A1 | 7/2004 | Bosch et al. | |
| 2004/0142921 A1 | 7/2004 | Lu et al. | |
| 2004/0147575 A1 | 7/2004 | Soldato | |
| 2004/0156899 A1 | 8/2004 | Louie-Helm et al. | |
| 2004/0156903 A1 | 8/2004 | Abrams et al. | |
| 2005/0032862 A1 | 2/2005 | Franc et al. | |

FOREIGN PATENT DOCUMENTS

| | | | |
|---|---|---|---|
| EP | 0708103 A1 | 4/1996 | |
| EP | 0726072 A2 | 8/1996 | |
| EP | 0726072 A3 | 8/1996 | |
| EP | 0747050 A1 | 12/1996 | |
| EP | 0752249 A2 | 1/1997 | |
| EP | 0752249 A3 | 1/1997 | |
| EP | 1145711 A1 | 10/2001 | |
| EP | 1275391 A1 | 1/2003 | |
| EP | 1382334 A1 | 1/2004 | |
| EP | 1393722 A2 | 3/2004 | |
| EP | 1393722 A3 | 3/2004 | |
| FR | 2659967 A1 | 9/1991 | |
| FR | 2665702 A1 | 2/1992 | |
| JP | 05-032661 A | 2/1993 | |
| JP | 05-132467 A | 5/1993 | |
| JP | 05-186431 A | 7/1993 | |
| JP | 05-213894 A | 8/1993 | |
| JP | 06-065207 A | 3/1994 | |
| JP | 08-333253 A | 12/1996 | |
| JP | 09-100240 A | 4/1997 | |
| JP | 10-279566 A | 10/1998 | |
| JP | 2003-048852 A | 3/2003 | |
| WO | WO 91/14679 A1 | 10/1991 | |
| WO | WO 92/10097 A1 | 6/1992 | |
| WO | WO 93/04046 A1 | 3/1993 | |
| WO | WO 94/09778 A1 | 5/1994 | |
| WO | WO 97/17064 A1 | 5/1997 | |
| WO | WO 99/55340 A1 | 11/1999 | |
| WO | WO 99/65500 A1 | 12/1999 | |
| WO | WO 99/67236 | * | 12/1999 |
| WO | WO 99/67236 A1 | 12/1999 | |
| WO | WO 00/02556 A1 | 1/2000 | |
| WO | WO 00/16773 A1 | 3/2000 | |
| WO | WO 00/37075 A1 | 6/2000 | |
| WO | WO 02/092081 A1 | 11/2002 | |
| WO | WO 03/035062 A1 | 5/2003 | |
| WO | WO 03/050110 A1 | 6/2003 | |

OTHER PUBLICATIONS

Canadian Intellectual Property Office, Examination Report in Canadian Patent Application No. 2,568,640 (Jul. 28, 2010).

Japanese Patent Office, Examination Report in Japanese Patent Application No. 2007-514218 (Jun. 22, 2010).

Government of India Patent Office, First Examination Report in Indian Patent Application No. 7846/DELNP/2006 (Sep. 13, 2011).

* cited by examiner

PHARMACEUTICAL COMPOSITION CONTAINING IRBESARTAN

PRIORITY CLAIM TO RELATED APPLICATION

This application claims priority to U.S. Provisional Application 60/577,427, filed Jun. 4, 2004.

FIELD OF THE INVENTION

This application relates to pharmaceutical compositions containing irbesartan, and to pharmaceutical compositions containing irbesartan and hydrochlorothiazide.

BACKGROUND OF THE INVENTION

Irbesartan is chemically described as 2-butyl-3-[[29-(1H-tetrazol-5-yl) [1,19-biphenyl]-4-yl]methyl]1,3-diazaspiro[4,4]non-1-en-4-one, also as 2-n-butyl-4-spirocyclopentane-1-[(2'-(tetrazol-5-yl)biphenyl-4-yl)methyl]-2-imidazolin-5-one, also as 2-butyl-3-[[2'-(1H-tetrazol-5-yl) [1,1'-biphenyl]-4-y]methyl]-1,3-diazaspiro[4,4]non-1-en-4-one. Its empirical formula is $C_{25}H_{28}N_6O$, and it has the following structure:

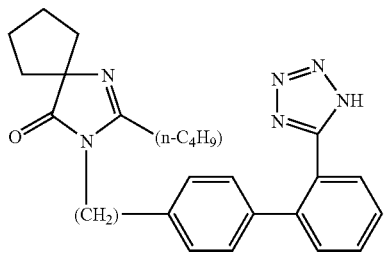

Irbesartan has a molecular weight of 428.5. The compound is described in U.S. Pat. No. 5,270,317, which is incorporated herein in its entirety.

In the United States, irbesartan is available for oral administration tablets containing 75 mg, 150 mg, or 300 mg of irbesartan, which are sold under the trade name AVAPRO. The drug also is formulated as 150 and 300 mg tablets that also include 12.5 mg hydrochlorothiazide, which are sold under the trade name AVALIDE.

As noted in U.S. Pat. No. 6,342,247, irbesartan is a fluffy material with relatively low bulk, and tap densities. In addition, irbesartan has certain undesirable flow characteristics. These properties make it difficult to formulate a large amount of the drug into a small tablet. Indeed, the '247 patent describes an oral formulation of irbesartan containing only up to 70% of the drug. Accordingly, there is a need for an improved formulation of irbesartan that contains a higher amount of the active ingredient.

SUMMARY OF THE INVENTION

This invention relates to pharmaceutical compositions comprising irbesartan, providing oral formulations with a high relative amount or concentration of irbesartan. In one embodiment, the present invention provides an oral formulation of irbesartan containing greater than 70% w/w irbesartan. In another embodiment, the invention provides an oral formulation of irbesartan which exhibits a dissolution profile according to which greater than about 85% of the irbesartan is dissolved within about 30 minutes, preferably greater than about 80% of the irbesartan is dissolved within about 10 minutes, using USP apparatus 2, placing the tablet in 1000 mL of 0.1N hydrochloric acid at 37° C. with paddle speed of 50 rpm. In another embodiment, the invention provides an oral formulation of two active pharmaceutical agents, irbesartan, and a diuretic, such as hydrochlorothiazide. These aspects and advantages, as well as additional inventive features, will be apparent upon reading the following detailed description. The formulations can optionally contain at least one additional active ingredient.

DETAILED DESCRIPTION OF THE INVENTION

The invention provides an oral formulation comprising irbesartan, and it provides an oral composition comprising irbesartan and hyhdrochlorothiazide. The irbesartan for inclusion in the inventive formulation can be manufactured according to any desired method, many of which are known to those of ordinary skill in the art. Examples of suitable methods to manufacture irbesartan are described in U.S. Pat. No. 5,270,317, which is incorporated herein in its entirety. Hydrochlorothiazide is also well known and can be manufactured by methods known in the art.

In one embodiment, the invention provides an oral formulation comprising irbesartan that includes at least about 70% irbesartan w/w. Preferably, the formulation includes at least about 75% w/w irbesartan, and more preferably the formulation includes from about 75% w/w to about 80% w/w irbesartan. A higher relative amount or concentration of irbesartan can be included, if desired.

In another embodiment, the invention provides an oral formulation comprising irbesartan which exhibits an improved dissolution profile according to the U.S. Pharmacopeia, using USP apparatus 2, placing the tablet in 1000 mL of 0.1N hydrochloric acid at 37° C. with paddle speed of 50 rpm. In some embodiments of the invention, the oral formulation comprising irbesartan exhibits a dissolution profile according to which greater than about 80% of the irbesartan is dissolved within about 10 minutes, and even more preferably greater than about 85% of the irbesartan is dissolved within about 10 minutes. The present invention provides, in another aspect, an oral formulation comprising irbesartan which exhibits a dissolution profile according to which at least about 75% of the irbesartan is dissolved within about 5 minutes, at least about 85% of the irbesartan is dissolved within about 10 minutes and at least about 95% of the irbesartan is dissolved in about 20 minutes. In accordance with another aspect of the invention, an oral formulation comprising irbesartan is provided which exhibits a dissolution profile according to which at least 97% of irbesartan is dissolved within 30 minutes. In some embodiments of the invention, the oral formulation comprising irbesartan exhibits a dissolution profile according to which greater than about 85% of the irbesartan is dissolved within about 30 minutes.

In addition to irbesartan, the oral formulation can include at least one additional active agent or combination of additional active agents. A preferred active agent to include in the formulation is a diuretic agent, such as hydrochlorothiazide, bendroflumethiazide, benzthiazide, chlorothiazide, chlorthalidone, cyclothiazide, hydroflumethiazide, methyclothiazide, metolazone, polythiazide, quinethazone, and trichlormethiazide. Preferably, at least one diuretic is a thiazidic such as chlorothiazide and hydrochlorothiazide. Hydrochlorothiazide, the 3,4-dihydro derivative of chlorothiazide, is the preferred diuretic for inclusion in the inventive composition. Its chemical name is 6-chloro-3,4-dihydro-2H-1,2,4-benzothiadiazine-7-sulfonamide 1,1-dioxide. Its empirical formula is $C_7H_8ClN_3O_4S_2$. Hydrochlorothiazide can be prepared by methods known to those of skill in the art The amount of diuretic, such as hydrochlorothiazide is included in the formulation can be varied to achieve the desired therapeutic effect. In a preferred embodiment, the amount of diuretic is from about 3% to about 7% by weight of the formulation, more preferably, 3.32 to about 6.65% by weight of the formulation. The preferred diuretic is hydrochlorothiazide.

In addition to irbesartan and optional additional active ingredient or combination of additional active ingredients, the formulation contains at least one pharmaceutically acceptable excipient. In this context, the term "excipient" refers to pharmaceutically acceptable chemicals known to those of ordinary skill in the art of pharmacy to aid the administration of the medicinal agent. Preferable excipients for inclusion in the inventive formulation include binders, surfactants, diluents, disintegrants, antiadherents, and lubricants.

Preferably, the inventive composition comprises, one or more binders. Suitable "binders" can be selected from those capable of facilitating granulation of the irbesartan into larger, denser, and more free-flowing particles. Preferred binders include povidone (most preferably employed in the range of 1.0-7.0% by weight), pregelatinized starch (most preferably employed in the range of 1.0-10.0% by weight), algenic acid (most preferably employed in the range of 1.0-7.0% by weight) or sodium alginate (most preferably employed in the range of 1.0-5.0% by weight), cellulose or cellulose derivatives such as carboxymethylcellulose sodium (most preferably employed in the range of 1.0-6.0% by weight), ethylcellulose (most preferably employed in the range of 1.0-4.0% by weight), hydroxyethyl cellulose (most preferably employed in the range of 1.0-5.0% by weight), hydroxypropyl cellulose (most preferably employed in the range of 1.0-7.0% by weight), hydroxypropyl methylcellulose (most preferably employed in the range of 1.0-6.0% by weight) or methylcellulose (most preferably employed in the range of 1.0-6.0% by weight), gelatin (most preferably employed in the range of 1.0-7.0% by weight). Other binders known to those of skill in the art can be employed. Preferably, the binder is povidone, most preferably, PVP K-30, and, where present, it can represent of from about 2.0% w/w to about 2.15% w/w, most preferably 2.13% w/w, of the formulation. Another preferred binder is pregelatinized starch, most preferably, starch 1500 and, where present, the pregelatinized starch (starch 1500) typically represents from about 6.35%, most preferably, 6.38% w/w, and about 8.0% w/w of the formulation.

The inventive composition preferably includes at least one disintegrant. Suitable "disintegrants" can be selected from one or more components, which facilitate the break up of a tablet prepared from the composition when placed in contact with an aqueous medium. Any suitable disintegrant can be employed within the inventive formulation. Preferred disintegrant are croscarmellose sodium, such as Ac-Di-Sol (most preferably employed in the range of 1.0-7.0% by weight), algenic acid (most preferably employed in the range of 1.0-7.0% by weight) or sodium alginate (most preferably employed in the range of 1.0-7.0% by weight), carboxymethylcellulose sodium (most preferably employed in the range of 1.0-7.0% by weight), crospovidone (most preferably employed in the range of 1.0-7.0% by weight), sodium starch glycolate (most preferably employed in the range of 1.0-7.0% by weight), pregelatinized starch (most preferably employed in the range of 1.0-7.0% by weight). Where present, preferably, croscarmellose sodium (Ac-Di-Sol) represents from about 3.15%, preferably 3.19%, w/w to about 5.0%, preferably 4.0%, w/w of the formulation.

The inventive composition preferably includes at least one surfactant. Suitable "surfactants" include compounds which aid in wetting so as to enhance dissolution. Any suitable surfactant can be employed in the inventive formulation. Preferred surfactants are sodium lauryl sulfate (most preferably employed in the range of 0.2-6.0% by weight), poly(oxyethylene), poly(oxypropylene) block co-polymers such as poloxamers, especially Poloxamer 188 (most preferably employed in the range of 0.2-6.0% by weight). Where present, the Poloxamer 188 typically represents from about 1.00%, preferably 1.06%, w/w to about 2.0% w/w of the formulation.

The formulation preferably includes one or more diluents. Suitable "diluents" include compounds which are capable of providing bulk to obtain a desired mass, such as desired tablet mass. Any suitable diluent can be employed in the inventive formulation. Preferred diluents are microcrystalline cellulose, such as Avicel PH 102 FMC, inorganic phosphates such as dibasic calcium phosphate, sugars such as lactose hydrous or lactose anhydrous and mannitol. Diluents are preferably included in the range of 2-10% by weight of the formulation. Where present, the microcrystalline cellulose typically represents from about 1% w/w to about 7.5% w/w of the formulation. For formulations that include only irbesartan as the active pharmaceutical agent, microcrystalline cellulose, where present, typically represents from about 1.9% w/w, to about 7.5% w/w of the formulation. For formulations which include irbesartan and diuretics, such as hydrochlorothiazide, as the active pharmaceutical agents, microcrystalline cellulose, when present, typically represents from about 1.9% w/w to about 6% w/w of the formulation. In some embodiments of the invention, microcrystalline cellulose, preferably is present in an amount of from about 1.97% w/w to about 5.3% w/w of the formulation, preferably 5.29% w/w. In other embodiments, microcrystalline cellulose preferably is present in an amount of from about 3.56% w/w to about 5.96% w/w of the formulation.

The inventive composition can further include at lease one antiadherent. Suitable "antiadherents" include compounds that contribute to the flowability of the formulation. Any suitable antiadherents can be employed in the inventive formulation. Preferred antiadherents are silicon dioxide, such as Syloid 244 (most preferably employed in the range of 0.2-2.0% by weight) or talc (most preferably employed in the range of 0.5-5.0% by weight). Where present, the silicon dioxide typically represents from about 0.4% w/w to about 0.5% w/w of the formulation.

The composition of the present invention preferably includes at least one lubricant. Suitable "lubricants" include compounds that assist in preparing the desired form of the formulation for administration, such as tabletting. Any suitable lubricant can be employed in the inventive formulation. Preferred lubricants are fatty acids or fatty acid derivatives such as calcium stearate (most preferably employed in the range of 0.5-2.0% by weight), glyceryl monostearate (most preferably employed in the range of 0.5-2.0% by weight), glyceryl palmitostearate (most preferably employed in the range of 0.5-2.0% by weight), magnesium stearate (most preferably employed in the range of 0.2-2.0% by weight), sodium lauryl sulfate (most preferably employed in the range of 0.5-2.0% by weight), sodium stearyl fumarate (most preferably employed in the range of 0.5-2.0% by weight), zinc stearate, stearic acid (most preferably employed in the range of 0.5-3.0% by weight), hydrogenated vegetable oil (most preferably employed in the range of 0.5-5.0% by weight), polyalkylene glycols such as polyethylene glycol (most preferably employed in the range of 1.0-5.0% by weight) talc (most preferably employed in the range of 1.0-5.0% by weight). Where present, the magnesium stearate represents from about 1.0% w/w to about 1.1% w/w of the formulation, preferably from about 1.0% w/w to about 1.06% w/w of the formulation.

Preferred compositions according to the invention is set forth in Table 1:

TABLE 1

| Preferred Ingredients | Component | Concentration Range (% w/w) |
| --- | --- | --- |
| Irbesartan | Active drug | 75-79.79 |
| Pregelatinized starch (starch 1500) | Binder | 6.38-8.0 |
| Povidone (PVP K-30) | Binder | 2-2.13 |
| Poloxamer 188 | Surfactant | 1.06-2.0 |
| Microcrystalline Cellulose (Avicel PH 102) | Diluent | 5.96-7.5 |
| Croscarmellose Sodium (Ac-Di-Sol) | Disintegrant | 3.19-4.0 |
| Silicon Dioxide (syloid 244) | Antiadherent | 0.43-0.5 |
| Magnesium Stearate | Lubricant | 1.0-1.06 |

The inventive formulation includes any form of irbesartan for oral administration, or any form of irbesartan and diuretic, such as hydrochlorothiazide, such as a tablet, caplet, capsule or the like. The preferred formulation is a tablet. Most preferably, tablets of the present invention contain (per tablet) 300 mg of irbesartan. The total weight of the tablet preferably is between 376 mg and 400 mg.

Formulations containing irbesartan can be prepared by any suitable method. A preferred method for forming a tablet formulation comprising irbesartan according to one embodiment of the present invention is by a wet granulation process. By way of example, the irbesartan formulation can be prepared according to the following method:

1. Irbesartan is partially granulated with granulating solution of povidone in purified water using high shear mixer.
2. Pregelatinized starch is mixed with the mixture of step 1 in high shear mixer.
3. The blend of step 2 is granulated with a granulating solution of Poloxamer 188 in purified water using high shear mixer.
4. The granules formed in step 3 are dried in fluid bed dryer.
5. The dried granules are sized by passing them through an oscillating granulator.
6. The milled dried granulate of step 5 is mixed with microcrystalline cellulose, croscarmellose sodium and silicon dioxide in a blender.
7. Magnesium stearate is added to the mixture of step 6 and mixed.
8. The mixture from step 7 is compressed to form tablets using a tablet press.

Formulations that include irbesartan and a diuretic, such as hydrochlorothiazide, can include binders such as povidone, without a surfactant, and they can include binders such as povidone and surfactant, such as poloxamer, preferably Poloxamer 188. In some preferred embodiments of the present invention, povidone comprises from about 2 to about 2.5% w/w and preferably 2.13% w/w of a composition comprising irbesartan and diuretic such as hydrochlorothiazide. In another preferred embodiment of a composition comprising irbesartan and diuretic such as hydrochlorothiazide according to the present invention, the composition comprises povidone in an amount of from about 2 to about 2.5% w/w, more preferably 2.13% w/w of the composition, and poloxamer of from about 1 to about 1.2% w/w, more preferably 1.06% w/w of the composition.

Formulations containing irbesartan and diuretic can be prepared by any suitable method. A preferred method for forming a tablet formulation comprising irbesartan and hydrochlorothiazide according to one embodiment of the present invention is by a wet granulation process. By way of example, a formulation comprising irbesartan and hydrochlorothiazide can be prepared according to the following method:

1. Irbesartan and hydrochlorothiazide are mixed using high shear mixer.
2. Pregelatinized Starch is mixed with the mixture of step 1 in high shear mixer.
3. The mixture from step 2 is granulated with granulating solution of povidone in purified water using high shear mixer.
4. The granules are dried in fluid bed dryer.
5. The dried granules are sized by using oscillating granulator.
6. The milled dried granulate is mixed with microcrystalline cellulose, croscarmellose sodium and silicon dioxide in a blender.
7. The mixture of step 6 is mixed with magnesium stearate as a lubricant.
8. The mixture from step 7 is mixed to form tablets using tablet press.

By way of further example, a formulation comprising irbesartan and hydrochlorothiazide can be prepared according to the following method:

1. Irbesartan and hydrochlorothiazide are mixed using high shear mixer.
2. The mixture of step 1 is partially granulated with a granulating solution of povidone in purified water using high shear mixer.
3. Pregelatinized Starch is mixed with the mixture of step 2 in high shear mixer.
4. The mixture from step 3 is granulated with granulating solution of Poloxamer 188 in purified water using high shear mixer.
5. The granules are dried in fluid bed dryer.
6. The dried granules are sized by using oscillating granulator.
7. The milled dried granulate is mixed with microcrystalline cellulose, croscarmellose sodium and silicon dioxide in a blender.
8. The mixture of step 7 is mixed with magnesium stearate as a lubricant.
9. The mixture from step 8 is mixed to form tablets using tablet press.

The tablets comprising irbesartan and hydrochlorothiazide prepared from the compositions of the present invention preferably contain (per tablet), 150 mg of irbesartan and 12.5 mg of hydrochlorothiazide, or 300 mg of irbesartan and 12.5 mg of hydrochlorothiazide. Typically, the total weight of the tablet comprising 150 mg of irbesartan and 12.5 mg of hydrochlorothiazide is 188 mg and the total weight of the tablet comprising 300 mg irbesartan and 12.5 mg hydrochlorothiazide is 376 mg to 400 mg.

Preferred compositions according to the invention comprising irbesartan and hydrochlorothiazide are as follows:

| Preferred Ingredients | Component | Concentration Range (% w/w) |
|---|---|---|
| Irbesartan | Active drug | 75.0–79.79 |
| Hydrochlorothiazide | Active drug | 3.32–6.65 |
| Pregelatinized starch (starch 1500) | Binder | 3.19–5.32 |
| Povidone (PVP K-30) | Binder | 2.0–2.13 |
| Microcrystalline Cellulose (Avicel PH 102) | Diluent | 3.56–5.96 |
| Croscarmellose Sodium (Ac-Di-Sol) | Disintegrant | 3.19–4.0 |
| Silicon Dioxide (syloid 244) | Antiadherent | 0.4–0.43 |
| Magnesium Stearate | Lubricant | 1.0–1.06 |

The following examples are presented to illustrate certain features of the invention, but these should not be understood to limit the scope of the invention.

EXAMPLE 1

This example illustrates the preparation of tablets containing 75% irbesartan.

Tablets containing irbesartan were prepared in three potencies using the composition of the present invention described in Table 2.

1. 75 mg irbesartan with a total weight of 100 mg per tablet.

2. 150 mg irbesartan with total weight of 200 mg per tablet.

3. 300 mg irbesartan with a total weight of 400 mg per tablet.

TABLE 2

| Ingredients | Component | Concentration (% w/w) |
|---|---|---|
| Irbesartan | Active drug | 75 |
| Povidone (PVP K-30) | Binder | 2.0 |
| Pregelatinized Starch (Starch 1500) | Binder | 8.0 |
| Poloxamer 188 | Surfactant | 2.0 |
| Microcrystalline Cellulose (Avicel PH 102) | Diluent | 7.5 |
| Croscarmellose Sodium (Ac-Di-Sol) | Disintegrant | 4.0 |
| Silicon Dioxide (syloid 244) | Antiadherent | 0.5 |
| Magnesium Stearate | Lubricant | 1.0 |
| Total | | 100.0 |

Using the above formulation, tablets were prepared by an aqueous wet granulation process, in accordance with the method described above. The partial granulation of irbesartan with granulating solution of povidone in purified water was carried out in a high shear mixer (Diosna). This mixture was mixed with pregelatinized starch and then granulated with the granulating fluid of Poloxamer 188 in purified water. The granules obtained were dried in a fluid bed dryer until the loss-on-drying (LOD) was 1.5% or less. The dried granules were passed through an oscillating granulator. The milled granulates were mixed with the microcrystalline cellulose, croscarmellose sodium and silicon dioxide in a blender. The blend obtained was then mixed with magnesium stearate. By compressing the mixture using tabletting equipment, tablets were prepared for each potency having the composition as shown in Table 3.

TABLE 3

| Ingredients | 75 mg potency (mg) | 150 mg potency (mg) | 300 mg potency (mg) |
|---|---|---|---|
| Irbesartan | 75.0 | 150.0 | 300.0 |
| Povidone (PVP K-30) | 2.0 | 4.0 | 8.0 |
| Pregelatinized Starch (Starch 1500) | 8.0 | 16.0 | 24.0 |
| Poloxamer 188 | 2.0 | 4.0 | 8.0 |
| Microcrystalline Cellulose (Avicel PH 102) | 7.5 | 15.0 | 30.0 |
| Croscarmellose Sodium (Ac-Di-Sol) | 4.0 | 8.0 | 16.0 |
| Silicon Dioxide (syloid 244) | 0.5 | 1.0 | 2.0 |
| Magnesium Stearate | 1.0 | 2.0 | 4.0 |
| Total tablet weight | 100.0 | 200.0 | 400.0 |

Tablets of each potency were tested for dissolution according to the U.S. Pharmacopeia, using USP apparatus 2 and placing the tablet in 1000 ml of 0.1 hydrochloric acid at 37° C. with paddle speed of 50 rpm. The dissolution results are set forth in Table 3A.

TABLE 3A

Dissolution Results In %

| Time In Minutes | % Dissolve | % Dissolve |
|---|---|---|
| 5 | 79 | 77 |
| 10 | 92 | 86 |
| 20 | 97 | 95 |
| 30 | 98 | 97 |

EXAMPLE 2

This example illustrates the preparation of tablets containing 80% irbesartan.

Tablets containing irbesartan were prepared in these potencies from the composition of present invention describe in Table 4.

75 mg irbesartan with a total weight of 94 mg per tablet.

150 mg irbesartan with a total weight of 188 mg per tablet.

300 mg irbesartan with a total weight of 376 mg per tablet.

TABLE 4

| Ingredients | Component | Concentration (% w/w) |
|---|---|---|
| Irbesartan | Active drug | 79.79 |
| Povidone (PVP K-30) | Binder | 2.13 |
| Pregelatinized Starch (Starch 1500) | Binder | 6.38 |
| Poloxamer 188 | Surfactant | 1.06 |
| Microcrystalline Cellulose (Avicel PH 102) | Diluent | 5.96 |
| Croscarmellose Sodium (Ac-Di-Sol) | Disintegrant | 3.19 |
| Silicon Dioxide (syloid 244) | Antiadherent | 0.43 |
| Magnesium Stearate | Lubricant | 1.06 |
| Total | | 100.0 |

Using the above formulation the tablets were prepared by a wet granulation process as a method analogous to that of Example 1. The composition of this formulation is presented in Table 5.

TABLE 5

| Ingredients | 75 mg potency (mg) | 150 mg potency (mg) | 300 mg potency (mg) |
|---|---|---|---|
| Irbesartan | 75.0 | 150.0 | 300.0 |
| Povidone (PVP K-30) | 2.0 | 4.0 | 8.0 |
| Pregelatinized Starch (Starch 1500) | 6.0 | 12.0 | 24.0 |
| Poloxamer 188 | 1.0 | 2.0 | 4.0 |
| Microcrystalline Cellulose (Avicel PH 102) | 5.6 | 11.2 | 22.4 |
| Croscarmellose Sodium (Ac-Di-Sol) | 3.0 | 6.0 | 12.0 |
| Silicon Dioxide (syloid 244) | 0.4 | 0.8 | 1.6 |
| Magnesium Stearate | 1.0 | 2.0 | 4.0 |
| Total tablet weight | 94.0 | 188.0 | 376.0 |

Tablets of each potency were tested for dissolution according to the U.S. Pharmacopeia, using USP apparatus 2 and placing the tablet in 1000 ml of 0.1 hydrochloric acid at 37° C. with paddle speed of 50 rpm. The % irbesartan in the formulation dissolved over time is set forth in Table 5A.

TABLE 5A

Dissolution Results In %

| Time In Minutes | % Dissolve | % Dissolve | % Dissolve |
|---|---|---|---|
| 5 | 79 | 80 | 84 |
| 10 | 93 | 90 | 95 |
| 20 | 100 | 96 | 99 |
| 30 | 102 | 98 | 99 |

EXAMPLE 3

This example illustrates the preparation of tablets comprising irbesartan in an amount of approximately 80% by weight of the formulation, and hydrochlorothiazide in an amount of approximately 3.32%-6.65% by weight of the formulation.

Tablets containing irbesartan and hydrochlorothiazide were prepared in various potencies in accordance with the present invention as described in Table 6.

The tablets a) comprise 150 mg irbesartan and 12.5 mg hydrochlorothiazide with a total weight of 188 mg per tablet and b) comprise 300 mg irbesartan and 12.5 mg hydrochlorothiazide with a total weight of 376 mg per tablet.

TABLE 6

| Ingredients | Component | Concentration (% w/w) | Concentration (% w/w) |
|---|---|---|---|
| Irbesartan | Active drug | 79.79 | 79.79 |
| Hydrochlorothiazide | Active drug | 6.65 | 3.32 |
| Pregelatinized Starch (Starch 1500) | Binder | 3.19 | 4.12 |
| Povidone (PVP K-30) | Binder | 2.13 | 2.13 |
| Microcrystalline Cellulose (Avicel PH 102) | Diluent | 3.56 | 5.96 |
| Croscarmellose Sodium (Ac-Di-Sol) | Disintegrant | 3.19 | 3.19 |
| Silicon Dioxide (syloid 244) | Antiadherent | 0.43 | 0.43 |
| Magnesium Stearate | Lubricant | 1.06 | 1.06 |
| Total | | 100.0 | 100.0 |

Using the above formulation, tablets were prepared by wet granulation. Irbesartan and hydrochlorothiazide were mixed in a high shear mixer (Diosna). This mixture was mixed with pregelatinized starch and then granulated with the granulating fluid of povidone in purified water. The granules obtained were dried in a fluid bed dryer until the loss-on-drying (LOD) is 1.5% or less. The dried granules were passed through an oscillating granulator. The milled granulates were mixed with the microcrystalline cellulose, croscarmellose sodium and silicon dioxide in a blender. The blend obtained was then mixed with magnesium stearate. By compressing the mixture using tabletting equipment, tablets were prepared for each potency having the composition as shown in the table above.

EXAMPLE 4

This example illustrates another formulation containing irbesartan and hydrochlorothiazide in accordance with the invention. The formulations were made by wet granulation, as described above.

TABLE 7

| Ingredients | 150 mg/12.5 mg potency (mg) | 300 mg/12.5 mg potency (mg) |
|---|---|---|
| Irbesartan | 150.0 | 300.0 |
| Hydrochlorothiazide | 12.5 | 12.5 |
| Pregelatinized Starch (Starch 1500) | 6.0 | 15.5 |
| Povidone (PVP K-30) | 4.0 | 8.0 |
| Microcrystalline Cellulose (Avicel PH 102) | 6.7 | 22.4 |
| Croscarmellose Sodium (Ac-Di-Sol) | 6.0 | 12.0 |
| Silicon Dioxide (syloid 244) | 0.8 | 1.6 |
| Magnesium Stearate | 2.0 | 4.0 |
| Total tablet weight | 188.0 | 376.0 |

EXAMPLE 5

This example illustrates another formulation containing irbesartan and hydrochlorothiazide in accordance with the invention. The formulations were made by wet granulation as described above.

TABLE 8

| Ingredients | 300 mg/12.5 mg potency (mg) | Concentration (% w/w) | 150 mg/12.5 mg potency (mg) | Concentration (% w/w) |
|---|---|---|---|---|
| Irbesartan | 300.0 | 79.79 | 150 | 79.79 |
| Hydrochlorothiazide | 12.5 | 3.32 | 12.5 | 6.65 |
| Pregelatinized Starch (Starch 1500) | 12.0 | 3.19 | 6.0 | 3.19 |

TABLE 8-continued

| Ingredients | 300 mg/12.5 mg potency (mg) | Concentration (% w/w) | 150 mg/12.5 mg potency (mg) | Concentration (% w/w) |
|---|---|---|---|---|
| Povidone (PVP K-30) | 8.0 | 2.13 | 4.0 | 2.13 |
| Microcrystalline Cellulose (Avicel PH 102) | 19.9 | 5.29 | 3.7 | 1.96 |
| Croscarmellose Sodium (Ac-Di-Sol) | 18.0 | 4.79 | 9.0 | 4.79 |
| Silicon Dioxide (syloid 244) | 1.6 | 0.43 | 0.8 | 0.43 |
| Magnesium Stearate | 4.0 | 1.06 | 2.0 | 1.06 |
| Total tablet weight | 376.0 | 100.0 | 188.0 | 100.0 |

EXAMPLE 6

This example illustrates another formulation containing irbesartan and hydrochlorothiazide in accordance with the invention. The formulations were made by wet granulation as described above.

TABLE 9

| Ingredients | 150 mg/12.5 mg potency (mg) | Concentration (% w/w) | 300 mg/12.5 mg potency (mg) | Concentration (% w/w) |
|---|---|---|---|---|
| Irbesartan | 150.0 | 79.79 | 300.0 | 79.79 |
| Hydrochlorothiazide | 12.5 | 6.65 | 12.5 | 3.32 |
| Pregelatinized Starch (Starch 1500) | 6.0 | 3.19 | 12.0 | 3.19 |
| Povidone (PVP K-30) | 4.0 | 2.13 | 8.0 | 2.13 |
| Poloxamer 188 | 2.0 | 1.06 | 4.0 | 1.06 |
| Microcrystalline Cellulose (Avicel PH 102) | 3.7 | 1.97 | 19.9 | 5.29 |
| Croscarmellose Sodium (Ac-Di-Sol) | 7.0 | 3.72 | 14.0 | 3.72 |
| Silicon Dioxide (syloid 244) | 0.8 | 0.43 | 1.6 | 0.43 |
| Magnesium Stearate | 2.0 | 1.06 | 4.0 | 1.06 |
| Total | 188.0 | 100.0 | 376.0 | 100.0 |

All references, including publications, patent applications, and patents, cited herein are hereby incorporated by reference to the same extent as if each reference were individually and specifically indicated to be incorporated by reference and were set forth in its entirety herein. Also, reference herein to other publications is not an admission that such publications constitute prior art to this application.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition comprising irbesartan a binder, and a surfactant wherein the irbesartan is at least 79.79% w/w of the total composition.

2. The composition of claim 1, wherein said composition exhibits a dissolution profile according to which greater than 85% of the irbesartan is dissolved within about 30 minutes using United States Pharmacopeia (USP) apparatus 2, placing the tablet in 1000 mL of 0.1N hydrochloric acid at 37° C. with paddle speed of 50 rpm.

3. The composition of claim 1, further wherein said composition comprises at least one diuretic agent.

4. The composition of claim 3, wherein the diuretic agent is hydrochlorothiazide.

5. The composition of claim 1, in the form of a tablet.

6. The composition of claim 1, in the form of the product of a wet granulation process.

7. The composition of claim 1, wherein the binder is povidone or pregelatinized starch.

8. The composition of claim 7, wherein the povidone is about 1.0% w/w to about 7.0% w/w of the composition.

9. The composition of claim 7, wherein the pregelatinized starch is about 1.0% w/w to about 10.0% w/w of the composition.

10. The composition of claim 1, wherein said composition comprises a disintegrant, a diluent, an antiadherent, and/or a lubricant.

11. The composition of claim 10, wherein the disintegrant is croscarmellose sodium, the diluent is microcrystalline cellulose, the antiadherent is silicon dioxide, and the lubricant is magnesium stearate.

12. The composition of claim 11, wherein the croscarmellose sodium is about 1.0% w/w to about 7.0% w/w of the composition.

13. The composition of claim 11, wherein the microcrystalline cellulose comprises about 2.0% w/w to about 10.0% w/w of the composition.

14. The composition of claim 11, wherein the silicon dioxide comprises about 0.4% w/w to about 0.5% w/w of the composition.

15. The composition of claim 11, wherein the magnesium stearate comprises about 0.2% w/w to about 2.0% w/w of the composition.

16. The composition of claim 1, wherein the surfactant is a polyethylene-polypropylene glycol co-polymer.

17. The composition of claim 16, wherein the polyethylene-polypropylene glycol co-polymer is about 0.2% w/w to about 6.0% w/w of the composition.

18. The composition of claim 1, wherein the surfactant is poloxamer 188.

19. The composition of claim 16, wherein the poloxamer 188 is about 0.2% w/w to about 6.0% w/w of the composition.

20. The composition of claim 1, wherein the composition comprises, by weight, 79.79% irbesartan, and the pharmaceutical excipients comprise, by weight, about 8.5% binder, about 5.9% diluent, about 3.1% disintegrant, about 1% surfactant, about 1% lubricant, and about 0.5% antiadherent; wherein said binder consists of pregelantinized starch and povidone; said diluent is microcrystalline cellulose, said disintegrant is croscarmellose sodium, said surfactant is poloxamer 188, said lubricant is magnesium stearate, and said antiadherent is silicon dioxide.

21. The composition of claim 20, wherein said composition is a tablet, such that the tablet exhibits a dissolution performance such that greater than 85% of the irbesartan contained therein dissolves within 30 minutes under the following conditions: USP apparatus 2, placing the tablet in 1000 mL of 0.1N hydrochloric acid at 37° C. with paddle speed of 50 rpm.

22. The composition of claim 1, wherein the composition comprises, by weight, 79.79% irbesartan, about 3% to about 7% hydrochlorothiazide, about 5.3% to about 7.5% binder, about 3.5% to about 6% diluent, about 3% to about 3.2% disintegrant, about 1% to about 1.1% lubricant, and about 0.4% to about 0.5% antiadherent; wherein said binder consists of pregelantinized starch and povidone; said diluent is microcrystalline cellulose, said disintegrant is croscarmellose sodium, said lubricant is magnesium stearate, said surfactant is poloxamer 188, and said antiadherent is silicon dioxide.

23. The composition of claim 1, wherein the composition comprises, by weight, about 79.79% irbesartan, about 2.13% povidone, about 6.38% pregelatinized starch, about 3.15% croscarmellose sodium, about 1.01% poloxamer 188, about 5.96% microcrystalline cellulose, about 1.01% magnesium stearate and about 0.43% silicon dioxide.

24. The composition of claim 1, wherein the composition comprises, by weight, about 79.79% irbesartan, about 3.3% hydrochlorothiazide, about 3.1% pregelatinized starch, about 2.1% povidone, about 5.3% microcrystalline cellulose, about 4.7% croscarmellose sodium, about 0.4% silicon dioxide and about 1% magnesium stearate.

25. The composition of claim 1, wherein said composition is a tablet, such that the tablet exhibits a dissolution profile according to which greater than 80% of the irbesartan is dissolved within about 10 minutes using USP apparatus 2, placing the tablet in 1000 mL of 0.1N hydrochloric acid at 37° C. with paddle speed of 50 rpm.

26. The composition of claim 1, wherein said composition is a tablet, such that the tablet exhibits a dissolution profile according to which about 75% of the irbesartan is dissolved within about 5 minutes, about 85% of the irbesartan is dissolved within about 10 minutes, and about 95% of the irbesartan is dissolved within about 20 minutes using USP apparatus 2, placing the tablet in 1000 mL of 0.1N hydrochloric acid at 37° C. with paddle speed of 50 rpm.

* * * * *